United States Patent
Biedermann et al.

(10) Patent No.: US 8,419,797 B2
(45) Date of Patent: Apr. 16, 2013

(54) IMPLANT FOR STABILIZING BONES OR VERTEBRAE

(75) Inventors: Lutz Biedermann, VS-Villingen (DE); Wilfried Matthis, Weisweil (DE); Martin Pabst, Donaueschingen (DE); Martin Meer, Vöhringen (DE); Manja Herzog, Bad Dürrheim (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 75 days.

(21) Appl. No.: 13/034,553

(22) Filed: Feb. 24, 2011

(65) Prior Publication Data

US 2011/0230969 A1 Sep. 22, 2011

Related U.S. Application Data

(60) Provisional application No. 61/308,940, filed on Feb. 27, 2010.

(30) Foreign Application Priority Data

Feb. 26, 2010 (EP) .................................... 10154844

(51) Int. Cl.
*A61F 2/44* (2006.01)
*A61B 17/80* (2006.01)
(52) U.S. Cl. ..................................... 623/17.16; 606/289
(58) Field of Classification Search .... 623/17.11–17.16; 606/301, 305, 246, 329, 247, 280, 289, 290
See application file for complete search history.

(56) References Cited

U.S. PATENT DOCUMENTS

| 7,618,456 | B2 | 11/2009 | Mathieu et al. |
| 7,857,839 | B2 * | 12/2010 | Duong et al. .................. 606/290 |
| 8,062,294 | B2 * | 11/2011 | Reynolds ........................ 606/60 |
| 2004/0068319 | A1 | 4/2004 | Cordaro |
| 2008/0249575 | A1 * | 10/2008 | Waugh et al. .................. 606/305 |
| 2009/0030520 | A1 | 1/2009 | Biedermann et al. |
| 2009/0287249 | A1 * | 11/2009 | Reynolds et al. ............. 606/246 |

FOREIGN PATENT DOCUMENTS

WO    WO 2008/118599 A1    10/2008

OTHER PUBLICATIONS

Extended European Search Report dated Jun. 18, 2010 for Application No. EP 10 15 4844, 6 sheets.

* cited by examiner

*Primary Examiner* — Pedro Philogene
(74) *Attorney, Agent, or Firm* — Christie, Parker & Hale, LLP

(57) ABSTRACT

An implant for stabilizing bones or vertebrae includes an implant body with at least a first hole and a second hole that can be fixed by a first screw and a second screw. Each of the screws includes a screw thread. Each of the holes has a threaded portion with an internal thread for cooperating with the screw thread, wherein the threaded portion of at least the first hole is formed of a flexible material. A guiding member that is a separate part is insertable into the implant body such that it is arranged at least partially within the first hole. The guiding member is configured to guide the first screw when the first screw is screwed through the threaded portion of the first hole. The second screw is spaced apart from the guiding member when the second screw is screwed through the threaded portion of the second hole.

24 Claims, 7 Drawing Sheets

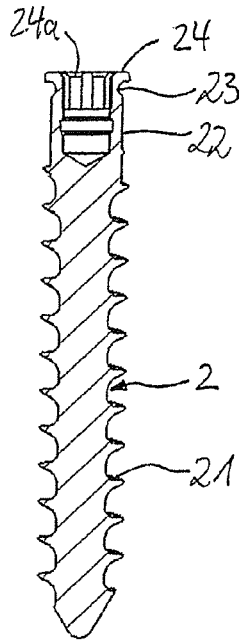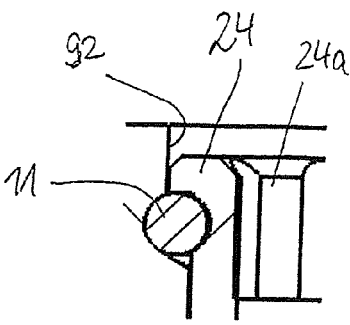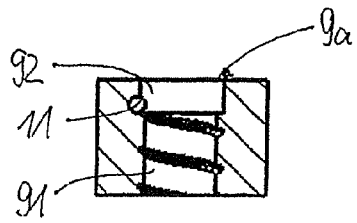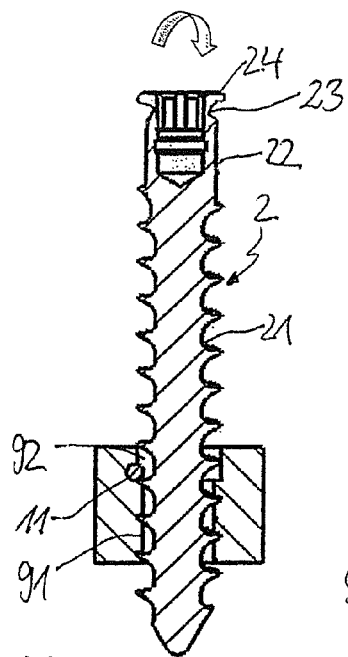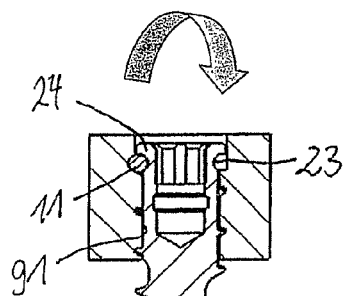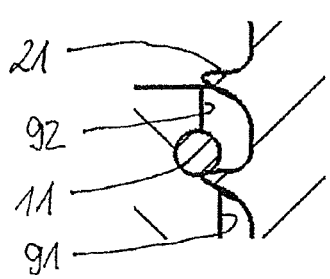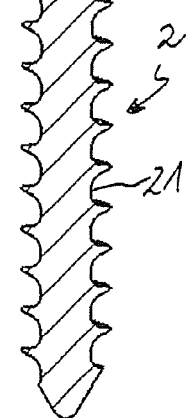

IMPLANT FOR STABILIZING BONES OR VERTEBRAE

CROSS-REFERENCE TO RELATED APPLICATION(S)

This Application claims priority to and the benefit of U.S. Provisional Application No. 61/308,940, filed Feb. 27, 2010, the entire contents of which are incorporated herein by reference. This Application also claims priority to and the benefit of EP 10 154 844.4, filed Feb. 26, 2010, the entire contents of which are incorporated herein by reference.

BACKGROUND

The invention relates to an implant for stabilizing bones or vertebrae. The implant comprises an implant body that is to be fixed by means of at least one screw to the bone or vertebra. The implant body has at least one hole with a threaded portion for receiving the bone screw. A guiding member is provided in the hole, which guides the screw when it is screwed through the threaded portion. In particular, the implant is an intervertebral cage or a bone plate, however, it can be any other implant that is to be fixed to a bone part of the human or animal body by means of a screw extending through a threaded hole.

An intervertebral implant in the form of a cage that is fixed to the adjacent vertebrae by means of screws is described, for example, in US 2009/0030520 A1. The cage can be made of a bio-compatible material such as Titanium or PEEK (polyetheretherketone).

If the cage is made of a bio-compatible plastic material, such as, for example PEEK, a problem may occur in that due to the greater flexibility of such a material compared to a metal, the bore hole for the screw may yield to some extent when the screw is screwed through the threaded portion. This may result in that the torque necessary for screwing the screw through the bore hole is considerably lower as compared to a metallic interconnection. In some clinical applications, for example, in the case of weak and/or osteoporotic bone substance, with such a low torque, there is only a reduced feed-back for the surgeon, which indicates to him how far the screw has already been advanced and whether the screw has the correct orientation.

U.S. Pat. No. 7,618,456 B2 describes an intervertebral implant in the form of a cage that can be made of any physiologically compatible material, preferably however, of an un-reinforced plastic. Un-reinforced plastic is said to be advantageous over fiber-reinforced plastics. Appropriate bone screws consisting of un-reinforced plastic of which the external threads exhibit load bevels of 11° to 14° may be used. Due to the relatively small slope of the load bevel high clamping forces can be achieved, as a result of which radial elongation and the danger of cracking of the plastic are reduced. Also, the bore hole may be in the form of a metal bush fitted with an inner thread for improving anchoring the bone screw in the plastic implant structure. The known implant may also consist partly of plastic and in the bore hole zones of metal.

SUMMARY

It is the object of the invention to provide an implant for stabilizing bones or vertebrae, in particular an intervertebral implant or a bone plate that provides an improved handling for the surgeon while simultaneously ensuring high safety.

The implant particularly can be made of a body-compatible plastic material, such as PEEK (polyetheretherketone), PEKK (polyetherketoneketone) or similar materials. Although these materials are more flexible than implants made of metal, the surgeon can use metal bone screws and obtain the necessary feed-back and locking force when screwing-in the bone screw.

With the guiding member according to the invention, the risk of misplacement of the bone screw is considerably reduced.

If the implant is made of a bio-compatible plastic material, such as, for example, PEEK or PEKK, which is not visible under irradiation with X-rays, the guiding member is visible under irradiation with X-rays, which is advantageous for examinations after surgery.

The guiding member can be provided even in the case wherein the hole in the implant body for the bone screw is very small.

Further features and advantages will become apparent from the description of embodiments of the invention by means of the accompanying drawings.

BRIEF DESCRIPTION OF THE DRAWINGS

FIG. 5 is a first step of inserting the screw in the hole wherein the hole is schematically shown as a straight hole.

FIG. 6A is a schematic view of a second step, in which the screw is screwed through the threaded portion of the hole.

FIG. 6B is an enlarged view of a portion of FIG. 6A.

FIG. 7A shows a third step in which the bone screw is fully screwed through the hole.

FIG. 7B is an enlarged portion of FIG. 7A.

DETAILED DESCRIPTION

Figure 1:
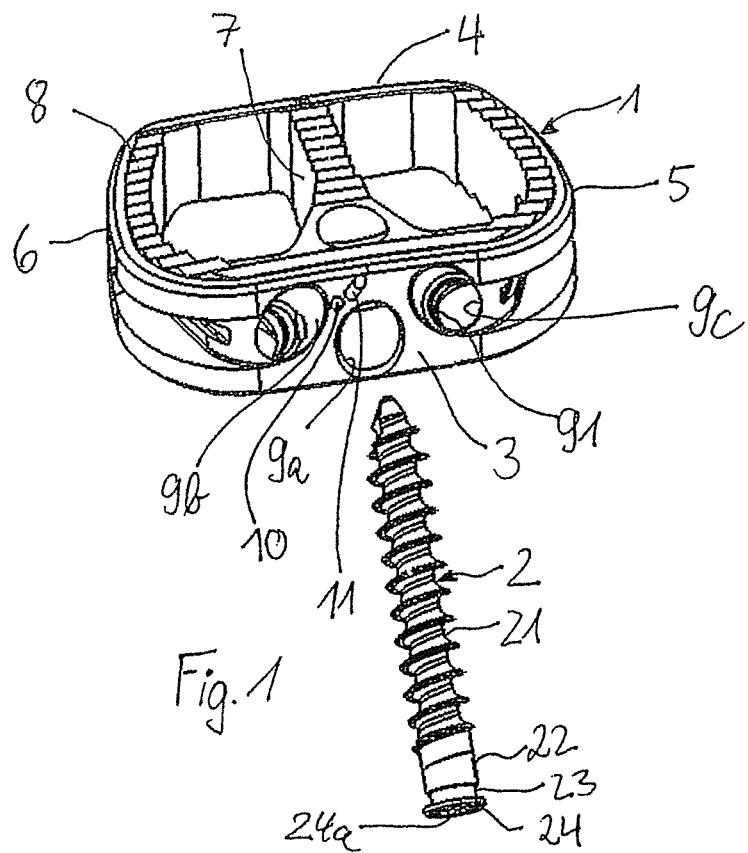
FIG. 1 is a perspective exploded view of an implant according to a first embodiment in the form of an intervertebral cage.
Figure 2:
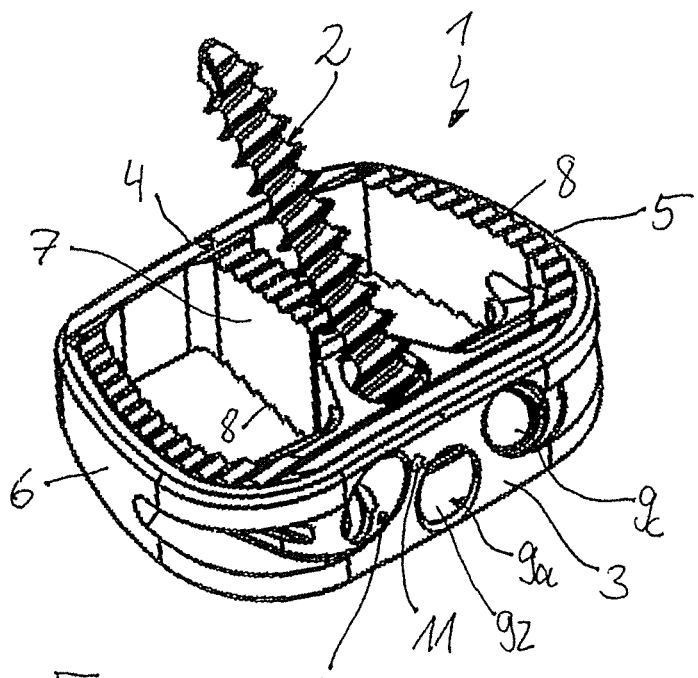
FIG. 2 is a perspective view of the cage of FIG. 1 with the bone screw passed through the respective hole.

The implant according to the first embodiment shown in FIGS. 1 and 2 includes an implant body 1 that can be fixed via bone screws 2 to adjacent vertebral bodies. The implant body is in the form of an anterior lumbar interbody fusion cage (ALIF-cage) that is to be introduced between two adjacent vertebrae of the lumbar spinal column from the anterior direction in order to replace an intervertebral disc. However, the implant can also be in the form of any other cage—like element suitable for replacing an intervertebral disc or a vertebrae that has been removed.

The implant body 1 has a front wall 3, a back wall 4, a right side wall 5 and a left side wall 6 that are integrally formed such that the right and the left side wall connect the front wall and the back wall. The front wall 3 represents an anterior wall and the back wall 4 represents a posterior wall of the implant body 1. Further, an inner wall 7 extends from the back wall 4 to the front wall 3 and connects them substantially in the middle between the right side wall 5 and the left side wall 6. The empty spaces between the side walls 5, 6 and the inner wall 7 may be filled with bone graft material.

Teeth 8 are provided on the top and bottom surfaces of the walls for facilitating an engagement with the end plates of the adjacent vertebral bodies. The contour of the implant body 1 along the front wall 3, the side walls 5, 6 and the back wall 4 is adapted to fill the space between the two adjacent vertebral bodies. Hence, in one embodiment, the width of the anterior front wall 3 is greater than the width of the posterior back wall 4 and the height of the implant body 1 increases from the back wall 4 in the direction of the front wall 3.

The implant body 1 further comprises at least one hole. In the embodiment shown, three holes 9a, 9b, 9c are provided in the front wall 3. A center hole 9a is provided substantially at the center between the left side wall 6 and the right side wall 5 and is inclined upwards. The center hole 9a extends also through a part of the inner wall 7. The side holes 9b, 9c are arranged at either side of the center hole 9a and are inclined downwards. The implant body is, however, not restricted to the implant body shown, it can have additional holes and/or holes with a different inclination. For example, four holes can also be provided in the front wall.

Figure 3:
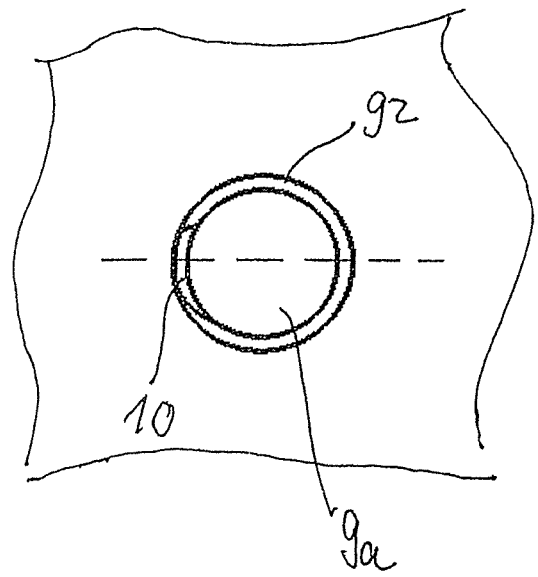
FIG. 3 is a schematic top view of a portion of the implant in the region of only the hole showing a portion of the pin hole for receiving the pin.
Figure 4:
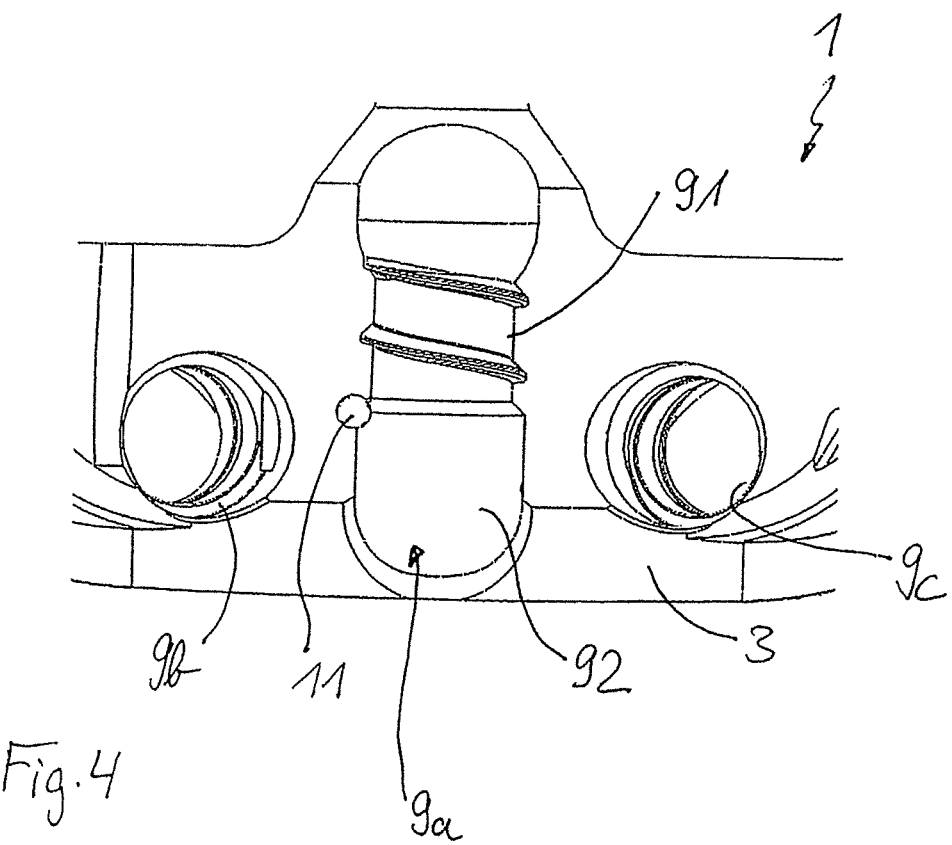
FIG. 4 shows a sectional view of the hole with the pin, the section being taken in a plane containing the thread axis of the hole.

As can been seen in particular in FIGS. 3 and 4, each of the holes 9a, 9b, 9c has a threaded portion 91 with an internal thread that cooperates with a screw thread. Further, a non-threaded portion 92 is provided between the threaded portion 91 and the surface of the front wall 3. The inner diameter of the non-threaded portion 92 is slightly larger than the outer diameter of the screw thread. A pin hole 10 is provided, which extends in such a way that it cuts a portion on the circumference of the non-threaded portion 92 as can be seen in FIGS. 3 and 4. The longitudinal axis of the pin hole 10 extends perpendicular to the thread axis of the threaded portion 91. A guiding member in the form of a pin 11 is inserted into the pin hole 10. In the embodiment shown, the pin 11 is substantially cylindrical. The pin 11 may have a roughened surface. The diameters of the pin 11 and of the pin hole 10 are such that when the pin 11 is inserted, it projects into the non-threaded portion 92 of the hole 9a like a secant of a circle but only to such an extent that it does not block the insertion of the screw 2. The pin 11 is configured to restrict the diameter of the non-threaded portion 92 in such a way so as to enhance the torque to be applied to the screw 2 when the screw 2 is screwed through the threaded portion 91. The restriction of the diameter is asymmetric in a plane perpendicular to the thread axis of the threaded portion 91.

Preferably, the pin 11 is arranged at a position in the non-threaded portion 92 that is adjacent to or close to the threaded portion 91.

In FIGS. 1 and 2 only the center hole 9a has the pin 11. However, also the side holes 9b, 9c may have a pin 11 as a guiding member.

The bone screw 2 has a threaded shaft 21 with a bone thread that cooperates with the internal thread of the threaded portion 91. Adjacent the threaded shaft 21, a non-threaded portion 22 is provided, which has an outer diameter that is slightly smaller than the inner diameter of the non-threaded portion 92 of the hole. Between the non-threaded portion 22 and an end portion 24 that has a recess 24a for engagement with a screw driver, a neck portion 23 having a reduced diameter is provided. The size of the neck portion 23 is such that it forms a groove for engagement with the pin 11.

Preferably, the material of the implant body is a bio-compatible plastic material, such as, for example, PEEK (polyetheretherketone) or PEKK (polyetherketoneketone). In particular, the threaded portion 91 is formed in the bio-compatible plastic material. The material of which the pin is made is preferably a bio-compatible metal such as Titanium, stainless steel or a suitable bio-compatible alloy, such as, for example, an Ni—Ti alloy, for example Nitinol; or a fiber re-inforced plastic material. Generally, the material of the implant body is more flexible than the material of the pin. For example, it has a lower modulus of elasticity and/or a lower tensile strength than the material of the pin. Any combinations of materials, not limited to the combination of plastic material and metal that have this relationship can be used. For example, the implant body can be made of a softer plastics and the pin can be made of a harder plastics.

The screw is usually made of a bio-compatible metal or reinforced plastic material as described above. It can be made of the same as or a different material from that of the pin. It can also be made of the same material as that of the implant body.

In use, once the implant body has been inserted between two adjacent vertebrae after removal of an intervertebral disc, the implant body is fixed by screwing the bone screws 2 through the respective holes into the end plates of the vertebral bodies.

The cooperation of the bone screw and the hole will now be described with reference to FIGS. 5 to 7, which show in a simplified schematic manner the insertion of the bone screw into a straight hole as compared to the inclined holes of the implant body shown in FIGS. 1 to 4. In a first step as shown in FIG. 5 a bone screw 2 of the appropriate length is selected and advanced into one of the holes 9a, 9b, 9c that has the pin 11 as a guiding member. Then, as shown in FIGS. 6A and 6B, the screw is screwed into the threaded portion 91. Thereby, the threaded portion 91 may widen to some extent due to the applied torque, if the implant body is made of a more flexible material. However, since the pin 11 restricts the diameter of the hole in such a way that the crests of the screw thread slide along the pin and snap behind it, the pin acts as a guiding and securing member. It prevents that the screw is screwed into the bone along the wrong trajectory if the material of the implant body yields during insertion of the screw. The pin also enhances the necessary torque to be applied during insertion. This provides a feed-back for the surgeon, in particular in a case in which the bone is weak and/or osteoporotic. The guiding function is also accomplished by a pre-stress or spring function exerted by the pin when the crests of the screw thread snap behind the pin.

When the screw has been fully inserted the pin snaps into the neck portion 23 of the screw and the end portion 24 abuts against the pin with its flat surface facing the pin and acting as a stop. In this condition, shown in FIGS. 7A and 7B, the abutment provides a feed-back to the surgeon that the screw has been fully inserted. Simultaneously, the screw is locked, since the pin rests in the neck portion 23.

Since the non-threaded portion 22 of the screw has a greater length than the threaded portion 91 of the hole, the implant body can be drawn against the bone. The threaded portion 91 prevents the screw from being pushed out backwards through the hole.

Figure 8:
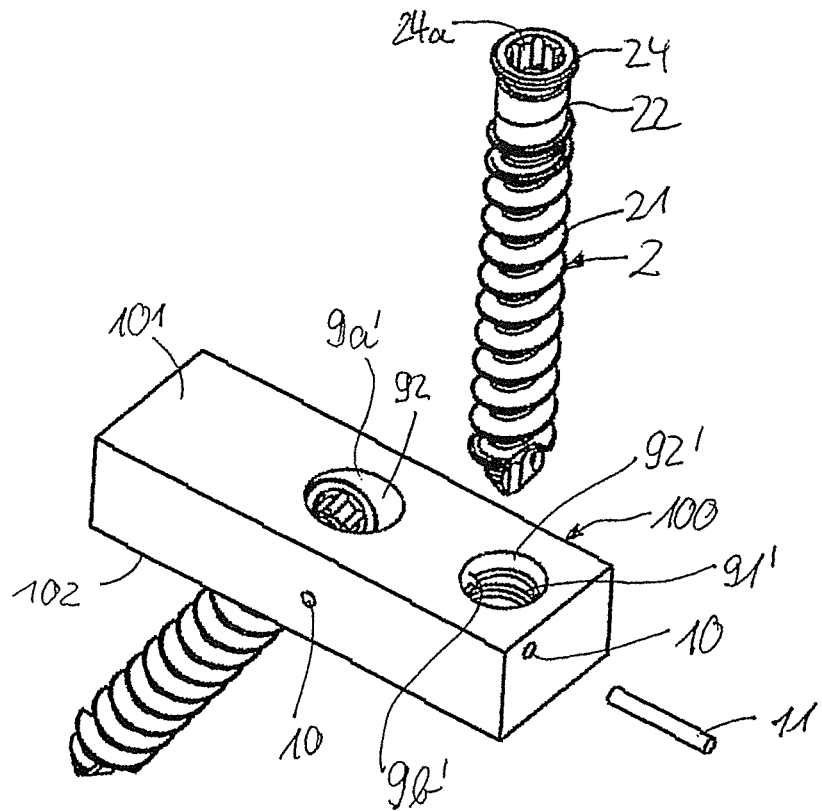
FIG. 8 is a perspective exploded view of a second embodiment of the implant in the form of a plate.
Figure 9:
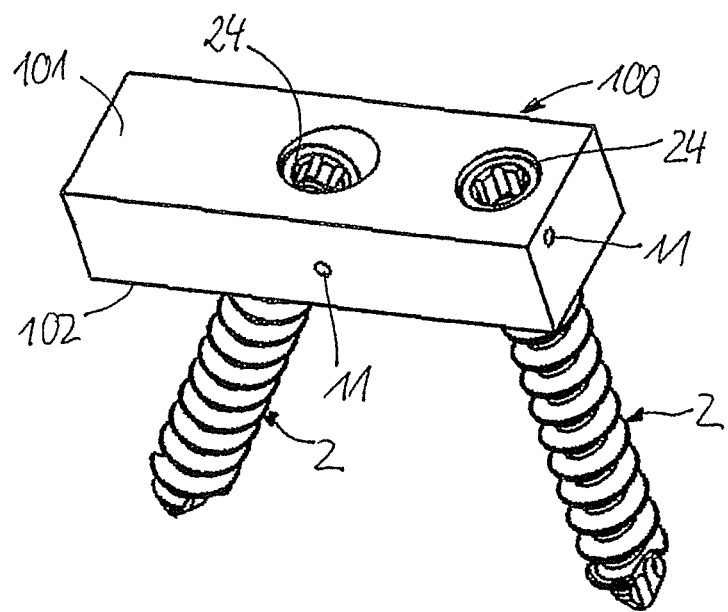
FIG. 9 is a perspective view of the implant of FIG. 8 with the bone screw screwed through the hole.

A second embodiment of the implant is shown in FIGS. 8 and 9. The implant body 100 is in the form of a bone plate. Parts of the second embodiment that are identical to that of the first embodiment are designated with the same reference numerals and the detailed description thereof is not repeated. The bone plate 100 has a generally rectangular shape, it is, however, not limited to such a rectangular shape. It has a top surface 101, a bottom surface 102 and a plurality of holes 9a', 9b', which extend from the upper surface 101 to the lower surface 102. In the specific embodiment depicted in the figures there is an inclined hole 9a' and a straight hole 9b'. The holes have the threaded portion 91' and the non-threaded portion 92' similar to the previous embodiment. Pin holes 10 are associated with each hole and pins 11 are inserted as in the previous embodiment. The guiding and feed-back function is the same as that of the previous embodiment.

Figures 10, 11:
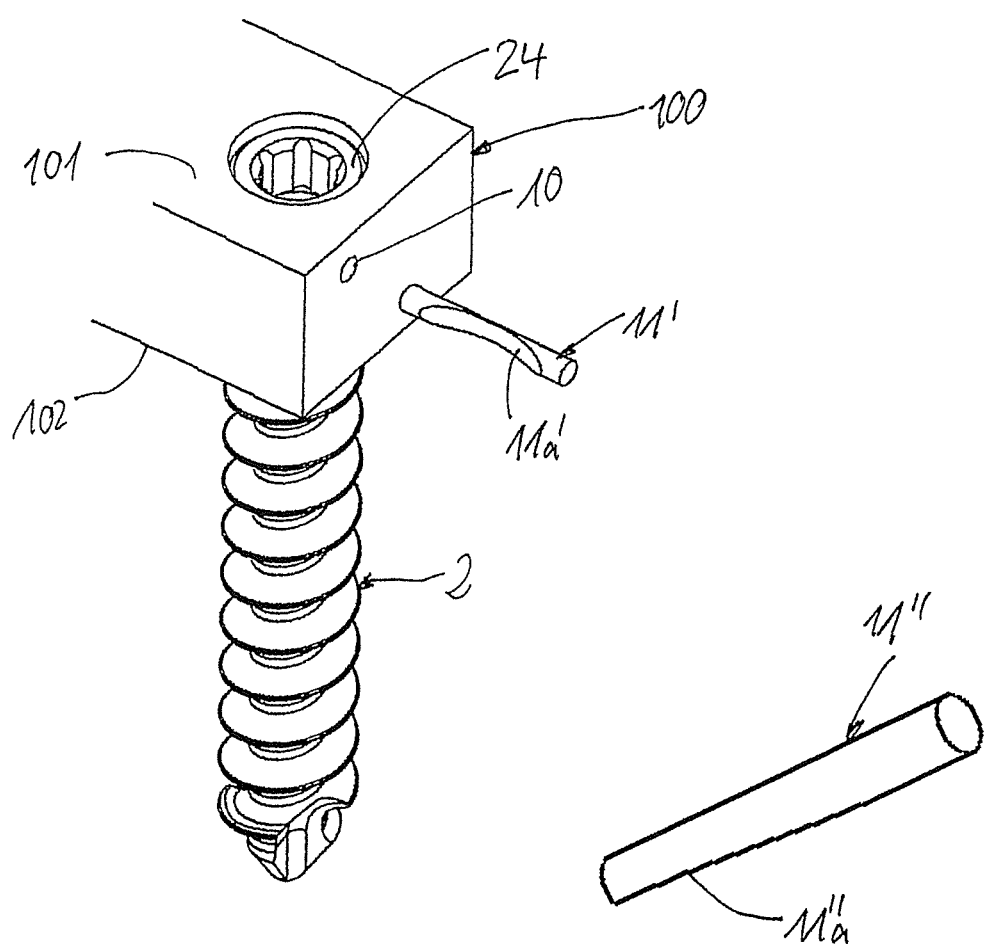
FIG. 10 is a perspective view of a modification of the first and second embodiment.
FIG. 11 is a perspective view of the pin according to a further modification.
Figure 12:
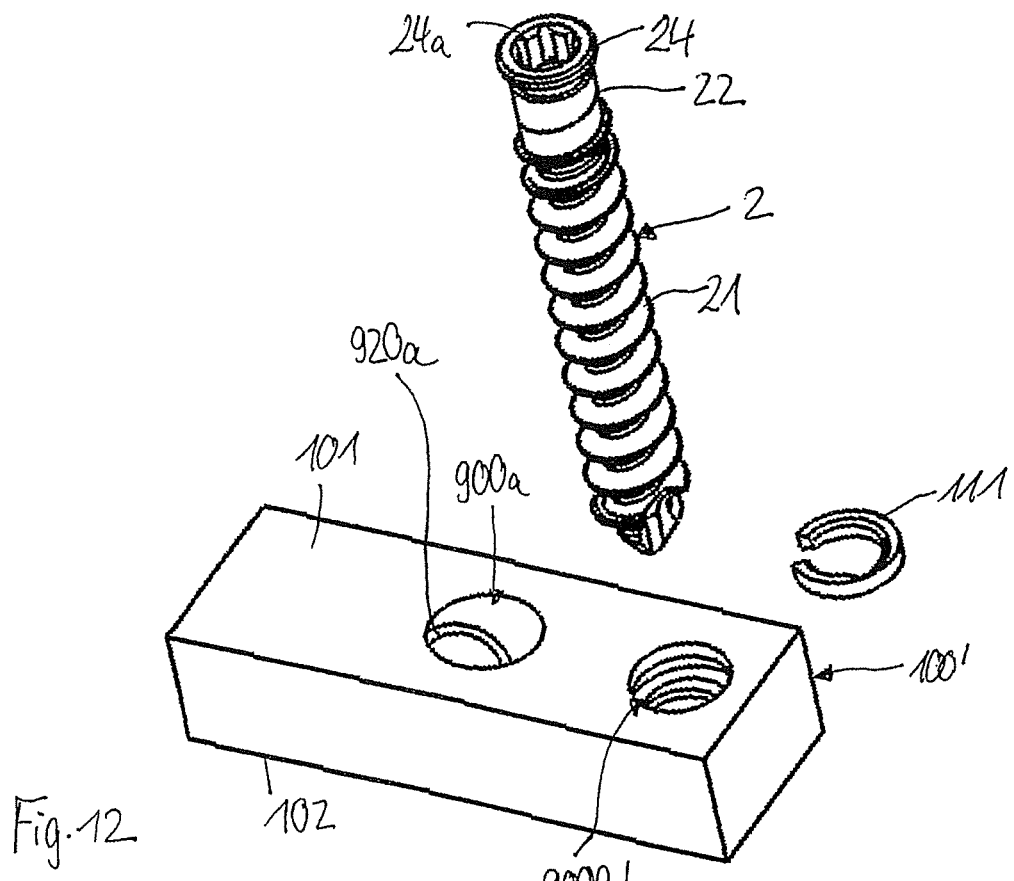
FIG. 12 is a perspective exploded view of a third embodiment of the implant in the form of a plate.
Figure 13:
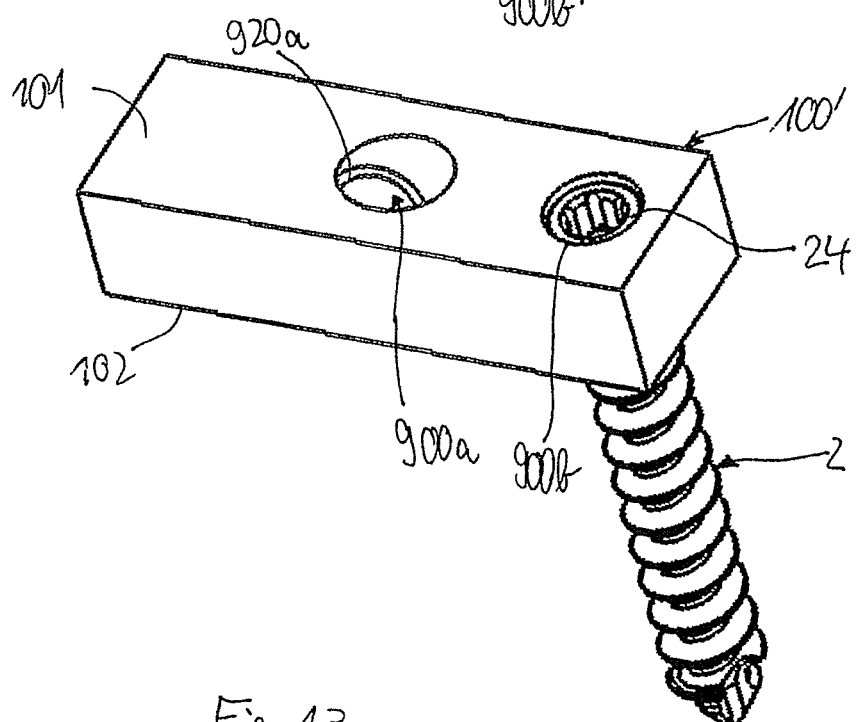
FIG. 13 is a perspective view of the implant of FIG. 12 with the bone screw screwed through the hole.
Figure 15:
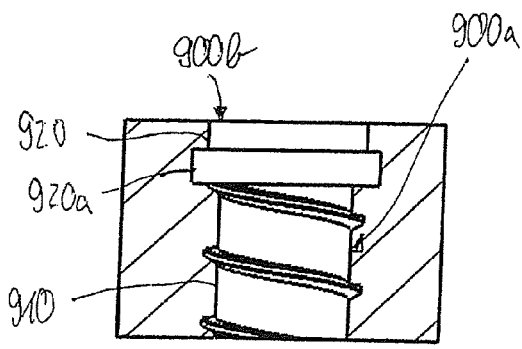
FIG. 15 is a sectional view of the hole without clip.
Figure 14:
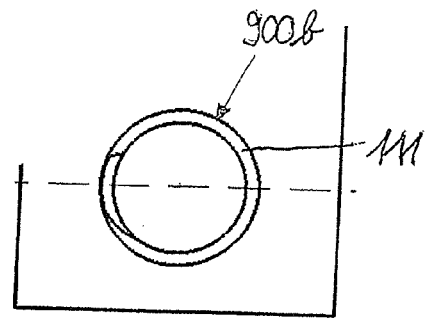
FIG. 14 is a top view of the hole of the third embodiment with the guiding clip inserted.
Figure 17:
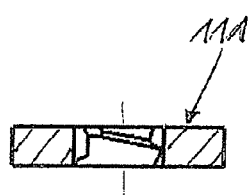
FIG. 17 is a sectional view of the clip along line B-B in FIG. 16.
Figure 16:
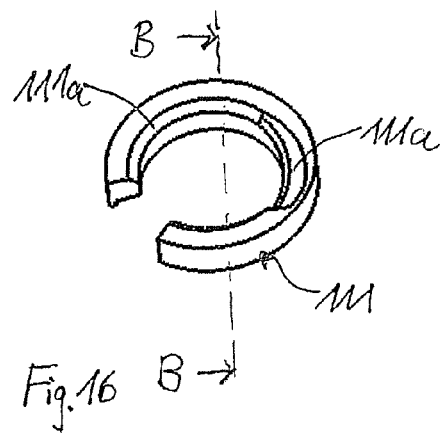
FIG. 16 is a perspective view of a clip that is to be inserted into the hole.
Figure 18:
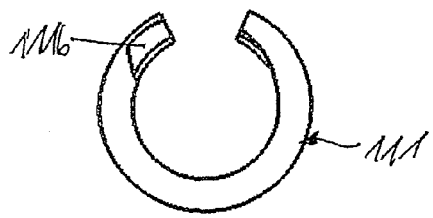
FIG. 18 is a bottom view of the clip.

A modification of the first and second embodiment is shown in FIGS. 10 and 11. It differs in that the pin 11' as shown in FIG. 10, has a thinned portion 11a at one of its sides that is substantially symmetrical with respect to the center of the pin. In a further modification, the pin 11" as shown in FIG. 11 has a thinned portion 11"a at one of its sides and only at one end. Other designs of thinned portions may also be contemplated. The pin 11',11" with such a thinned portion has some resiliency and can compensate tolerances of the pin, the screw and the hole.

A third embodiment will now be described with reference to FIGS. 12 to 18. The implant body of the third embodiment is a bone plate 100' as in the second embodiment. It has a top surface 101 and a bottom surface 102 and holes 900a and 900b. The third embodiment differs from the previous embodiments in that the guiding member is a circular member instead of a straight pin. The guiding member shown in FIGS. 14 to 18 is a substantially circular clip 111 that has a slot and two open ends, like a snap ring. Further, the clip may have a recess 111a at the top side and a recess 111b at the bottom side, which are similar to a portion of a turn of an internal thread and which facilitate screwing-through of the bone screw 2. The non-threaded portion 920 of the hole comprises a circular groove 920a with an enlarged diameter, which is adjacent to the threaded portion 910 in the embodiment shown in FIG. 15. The groove 920a serves to accommodate the clip 111. The size of the groove 920a and of the clip 111 is such that when the clip is inserted under pretension and has expanded in the groove 920a, it restricts the diameter of the non-threaded portion 920 in such a way that the torque necessary for inserting the screw 2 is increased. Thereby, the clip provides a guiding and feed-back function similar to the previous embodiments. The clip 111 is made of a less flexible material than the material of the implant body, such as of a metal. In use, the clip 111 is first inserted into the groove. Then, the screw is introduced and screwed through the clip and the threaded portion of the hole. The clip guides the screw such that the torque to be applied is enhanced. Finally, the clip acts as a stop for the end portion of the screw and also secures the screw from being pushed out.

If the guiding member according to the embodiments is formed of a metal, it is visible under X-ray irradiation even if the implant body itself is not visible.

The invention is not limited to the above described embodiments. Modifications can be contemplated. For example, many different types of plates and cages can be contemplated.

Also, the shape of the bone screw is not limited to the bone screw shown in the embodiments. Many different types of bone screws can be used. The guiding member can also have another shape. The threaded portion of the hole may be provided with a double or higher lead thread and two or more pins may be provided.

The invention claimed is:

1. An implant for stabilizing bones or vertebrae, the implant comprising:
   an implant body configured to be fixed to the bone or to a vertebra by means of at least a first screw comprising a screw thread,
   wherein the implant body comprises a first hole comprising a threaded portion with an internal thread for cooperating with the screw thread, wherein the threaded portion of the first hole is formed of a first material; and
   a guiding member that is a separate part and is insertable into the implant body such that it is arranged at least partially within the first hole,
   wherein the first material is more flexible than the material of the guiding member.

2. The implant of claim 1, wherein the threaded portion of the first hole is formed of a bio-compatible plastic material.

3. The implant of claim 1, wherein the first hole has at least one non-threaded portion and wherein the non-threaded portion has a section with an enlarged diameter that is larger than the outer diameter of the threaded portion and wherein the guiding member is located in the section with the enlarged diameter.

4. The implant of claim 1, wherein the guiding member is configured to restrict the diameter of the first hole to a diameter that is the same or slightly smaller than the inner diameter of the threaded portion at least one position.

5. The implant of claim 3, wherein the non-threaded portion is arranged before the threaded portion in the insertion direction of the screw into the first hole.

6. The implant of claim 1, wherein the guiding member is configured and arranged to enhance the torque to be applied when the first screw is screwed through the threaded portion.

7. The implant of claim 1, wherein the guiding member is a straight member.

8. The implant of claim 1, wherein the guiding member is a pin configured to at least partially project into the first hole.

9. The implant of claim 8, wherein the pin is configured to fit into a pin hole having a longitudinal axis perpendicular to the thread axis of the threaded portion of the first hole.

10. The implant of claim 1, wherein the guiding member is a curved member having two free ends.

11. The implant of claim 1, wherein the guiding member is a generally circular clip.

12. The implant of claim 3, wherein the guiding member is a generally circular clip, and wherein the non-threaded portion comprises a circular groove in which the circular clip is held under pre-stress.

13. The implant of claim 1, wherein the implant body is made of a material that is more flexible than the material of the guiding member.

14. The implant of claim 1, wherein the guiding member is made of a material that is less flexible than the material of the implant body.

15. The implant of claim 1, wherein the first screw is made of a material that is less flexible than that of the implant body.

16. The implant of claim 1, wherein the first screw comprises an end portion configured to abut against the guiding member when the first screw is fully inserted.

17. The implant of claim 1, wherein the implant is an intervertebral implant.

18. The implant of claim 1, wherein the implant is a bone plate.

19. The implant of claim 13, wherein the implant is made of a bio-compatible plastic material.

20. The implant of claim 19, wherein the implant is made of polyetheretherketone or polyetherketoneketone.

21. The implant of claim 14, wherein the guiding member is made of a bio-compatible metal.

22. The implant of claim 21, wherein the guiding member is made of titanium, a titanium alloy, nitinol, or stainless steel.

23. The implant of claim 16, wherein the first screw comprises a recessed portion in which the guiding member rests so that the first screw is locked in the hole.

24. The implant of claim 1, wherein the implant body further comprises a second hole comprising a threaded portion with an internal thread for cooperating with a screw thread of a second screw,
- wherein the guiding member is configured to guide the first screw when the first screw is screwed through the threaded portion of the first hole,
- wherein the second screw is spaced apart from the guiding member when the second screw is screwed through the threaded portion of the second hole.

* * * * *

UNITED STATES PATENT AND TRADEMARK OFFICE
CERTIFICATE OF CORRECTION

PATENT NO.         : 8,419,797 B2                                         Page 1 of 1
APPLICATION NO.    : 13/034553
DATED              : April 16, 2013
INVENTOR(S)        : Lutz Biedermann et al.

It is certified that error appears in the above-identified patent and that said Letters Patent is hereby corrected as shown below:

In the Claims

Column 6, Claim 4, line 33           After "portion"
                                     Insert -- at --

Signed and Sealed this
Twenty-fifth Day of February, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,419,797 B2
APPLICATION NO. : 13/034553
DATED : April 16, 2013
INVENTOR(S) : Biedermann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 57 days.

Signed and Sealed this
Twelfth Day of August, 2014

Michelle K. Lee
*Deputy Director of the United States Patent and Trademark Office*